United States Patent [19] [11] Patent Number: 6,074,379
Prichard [45] Date of Patent: *Jun. 13, 2000

[54] CATHETER STRAIN RELIEF DEVICE

[75] Inventor: James B. Prichard, St. Peters, Mo.

[73] Assignee: Sherwood Services AG, Schaffhausen, Switzerland

[*] Notice: This patent is subject to a terminal disclaimer.

[21] Appl. No.: 09/036,498

[22] Filed: Mar. 6, 1998

[51] Int. Cl.⁷ ................................................. A61M 25/00
[52] U.S. Cl. .......................... 604/524; 604/523; 604/177; 604/180; 285/114
[58] Field of Search ..................... 604/174–180, 604/523, 524, 264, 164–169, 280–284, 239–243; 285/417, 114–116, 235, 915, 178, 382; 138/106, 104–110, 120; 156/158, 292, 294–295, 305; 439/449

[56] References Cited

U.S. PATENT DOCUMENTS

| 3,097,646 | 7/1963 | Scislowicz | 128/214 |
|---|---|---|---|
| 3,191,655 | 6/1965 | McCord | 152/427 |
| 3,469,579 | 9/1969 | Hubert | 128/214.4 |
| 3,720,210 | 3/1973 | Diettrich | 128/214.4 |
| 3,721,231 | 3/1973 | Hubert | 128/2.05 R |
| 3,802,433 | 4/1974 | Raven | 128/214.4 |
| 3,861,972 | 1/1975 | Glover et al. | 156/86 |
| 4,191,185 | 3/1980 | Lemieux | 128/214.4 |
| 4,211,741 | 7/1980 | Ostoich | 264/173 |
| 4,292,970 | 10/1981 | Hession et al. | 128/214.4 |
| 4,354,495 | 10/1982 | Bodicky | 128/348 |
| 4,389,210 | 6/1983 | Genese | 604/177 |
| 4,391,029 | 7/1983 | Czuba et al. | 29/450 |
| 4,592,749 | 6/1986 | Ebling et al. | 604/283 |
| 4,610,674 | 9/1986 | Suzuki et al. | 604/282 |
| 4,776,849 | 10/1988 | Shinno et al. | 604/283 |
| 4,781,703 | 11/1988 | Walker et al. | 604/264 |
| 4,806,182 | 2/1989 | Rydell et al. | 156/211 |
| 4,840,622 | 6/1989 | Hardy et al. | 604/264 |
| 4,846,812 | 7/1989 | Walker et al. | 604/264 |
| 4,966,588 | 10/1990 | Rayman et al. | 604/165 |
| 4,991,629 | 2/1991 | Ernesto et al. | 138/89 |
| 5,030,205 | 7/1991 | Holdaway | 604/164 |
| 5,041,097 | 8/1991 | Johnson | 604/167 |
| 5,167,647 | 12/1992 | Wijkamp et al. | 604/95 |
| 5,330,449 | 7/1994 | Prichard et al. | 604/282 |

FOREIGN PATENT DOCUMENTS

| 0 168 289 | 1/1986 | European Pat. Off. | A61M 25/02 |
|---|---|---|---|
| 0 368 377 | 5/1990 | European Pat. Off. | A61M 39/02 |
| 0 434 324 A1 | 6/1991 | European Pat. Off. | A61M 25/00 |
| 1125735 | 6/1955 | France . | |
| 2033068 | 11/1970 | France . | |

Primary Examiner—Wynn Wood Coggins
Assistant Examiner—Eric Kline
Attorney, Agent, or Firm—Richard D. Allison; Douglas E. Denninger

[57] ABSTRACT

The present invention is generally directed to a strain relief device which assists in resisting bending and/or torsional forces while at the same time resisting axial pull forces to avoid separation of the strain relief device from the catheter tube during use. By way of example, the strain relief device of the present invention preferably includes an elongate body formed of an elastomeric material having a lumen formed therethrough along its entire length. The strain relief device lumen may be generally divided into proximal, central and distal portions which may each be of varying and/or different diameters. The strain relief device is preferably placed about a selected portion of the catheter tube, and the proximal and distal portions are bonded to the catheter tube. The inner diameter of the proximal portion may be approximately equal to the inner diameter of the distal portion and the central section has an inner diameter which is significantly larger than the inner diameter of either the distal or proximal portion of the strain relief device. Additionally, the inner diameter of the distal and proximal portions of the strain relief device are only slightly larger than the outer diameter of the catheter tube, and each of the distal and proximal portions includes one or more vent areas to allow air to escape from the central section while the bonding material flows into the proximal and distal portions of the strain relief device.

21 Claims, 3 Drawing Sheets

CATHETER STRAIN RELIEF DEVICE

FIELD OF THE INVENTION

This invention relates generally to strain relief devices for tubular members such as catheters and more particularly to an improved strain relief device for use on the body of a catheter. Even more specifically, the preferred form of the present invention relates to an improved strain relief device for use on tubing having two bonding sites.

BACKGROUND OF THE INVENTION

Catheters of the prior art are generally formed of three main elements. A first element is typically the elongated catheter tube. The elongated catheter tube is typically of sufficient length so that the distal end thereof may be positioned near the desired location in a patient while the proximal end thereof remains outside of the patient to allow for the delivery and/or removal of the desired fluids therethrough. A second element of the catheter is generally referred to as a catheter hub. The catheter hub is used to provide for the connection of a fluid delivery or fluid receipt or removal system to the catheter in a manner which is well known in the art. The final element of the catheter is the catheter tip. The catheter tip may be formed of various materials and may have a variety of configurations depending on the intended use of the catheter and the desired position of the catheter tip in the body of the patient.

Strain relief devices have been used in the past to prevent the collapse of a tube when it is subject to lateral (bending) forces. The strain relief device is designed to prevent non-uniform curvature (kinking) of the catheter tube at or near the junction of the hub and catheter tube. Strain relief devices of this type are typically attached to a catheter at a single bonding point or insert molded such that the flexible catheter tube is connected to the more rigid hub at a single stress point. This positioning of the strain relief device prevents bending forces from concentrating at the junction of the hub and catheter tube due to the non-uniform flexibility at the junction. The strain relief device is designed to spread the bending forces along a significant length of the catheter tube and away from the junction of the hub and catheter tube.

Although strain relief devices have previously functioned adequately to relieve the strain of bending forces at the junction of the hub and catheter tube, they have nevertheless been less than adequate to aid in strengthening the junction against axial forces, i.e., forces along the longitudinal axis of the catheter tube which tend to pull the catheter tube away from the hub. Such forces can arise either during normal use, or during any number of common accidents or mishaps. Forces exceeding the strength of the junction of the hub and catheter tube can lead to separation of the hub and catheter tube with disastrous consequences. An example of a strain relief device is disclosed in U.S. Pat. No. 5,330,449 granted to Prichard et al. and assigned to the Assignee of the present invention.

An additional area of a catheter which is prone to kinking or bending forces is the area of the catheter tube which is adjacent to the suture wing. Typically, the suture wing is formed as part of the hub or is located distally along the catheter tube at a location spaced apart from the hub. In the latter situation, the suture wing will be bonded at a single location along the catheter tube and may be a frequent location of catheter kinking when the suture wing is sutured to the skin of the patient. Additionally, when a patient has a suture wing attached to their skin, a common location for kinking is the portion of the catheter tube between the suture wing and the incision site. In this situation, patient movement of their arm, neck or leg may cause axial and longitudinal forces to be applied to the portion of the catheter tube between the suture wing and the incision site depending on the catheter location.

Catheters are routinely manufactured in large quantities and selected catheters are routinely tested for the strength of the bond at the junction of the hub and catheter tube in order to verify that a predetermined minimum allowable pull to separation force is met by the manufactured catheter. For safety reasons, it is critical that the catheters meet the separation forces which routinely occur during normal use of the catheter. Therefore, if a single catheter fails to pass the testing, the entire lot must be scrapped or reworked. Therefore, it is critical that the catheter be manufactured using reliable and consistent components and manufacturing processes.

Therefore, there exists a need in the art to develop a strain relief device which not only functions to relieve strain at the junction of the hub and catheter tube due to bending or torsional forces, but also to relieve strain on the catheter tube due to axial pulling forces, preventing the inadvertent separation of the affected portion of the catheter. Additionally, there exists a need to develop a catheter and manufacturing process in which the catheter consistently meets the minimum pull strength requirements as well as the requirement for a reliable and easily reproducible end product.

OBJECTS OF THE INVENTION

It is an object of the present invention to provide a strain relief device which is capable of resisting bending, torsional and axial forces generated along a catheter tube.

It is another object of the present invention to provide a strain relief device which maximizes catheter strength by providing uniform distribution of stresses about the catheter tube that might result from bending, twisting or axial pulling forces.

It is yet another object of the present invention to provide a strain relief device which is symmetrically bonded to a catheter tube to evenly distribute stresses due to bending, twisting or axial pulling forces around the catheter tube.

It is also an object of the present invention to provide a strain relief device which is capable of drawing the bonding material between the strain relief device and the catheter tube in a uniform and symmetrically shaped manner.

It is a further object of the present invention to provide a strain relief device which provides added resistance against axial pull forces while at the same time maintaining a predetermined flexibility and deflection characteristic for resisting the concentration of bending or twisting forces at the intersection of the strain relief device and the catheter tube.

SUMMARY OF THE INVENTION

The present invention is generally directed to a strain relief device which assists in resisting bending and/or torsional forces while at the same time resisting axial pull forces to avoid separation of the strain relief device from the catheter tube during use.

In a preferred embodiment, by way of example and not necessarily by way of limitation, the strain relief device of the present invention preferably includes an elongate body formed of an elastomeric material having a lumen formed therethrough along its entire length. The strain relief device lumen may be generally divided into proximal, central and distal portions which may each be of varying and/or different diameters. The device of the present invention is preferably placed about a selected portion of the catheter tube and the proximal and distal portions are bonded to the catheter tube. In the preferred embodiment, the inner diameter of the proximal portion is approximately equal to the inner diameter of the distal portion and the central section has an inner diameter which is significantly larger than the inner diameter of either the distal or proximal portion of the strain relief device. Additionally, the inner diameter of the distal and proximal portions of the strain relief device are only slightly larger than the outer diameter of the catheter tube and each of the distal and proximal portions includes one or more vent areas to allow air to escape from the central section while the bonding material flows into the proximal and distal portions of the strain relief device. The exterior of the preferred form of the present invention is preferably formed as a suture wing. The suture wing preferably has a pair of laterally extending wing members with openings therein for sutures to pass therethrough for attachment of the suture wing to the body of the patient.

In a second preferred form of the present invention, the strain relief device may be used to relieve the bending, twisting and axial stresses on a portion of a catheter assembly wherein the diameter of the catheter is in transition or where two tubes of different diameters are joined resulting in a catheter assembly having different proximal and distal diameters. For example, a catheter formed as bump tubing wherein the outer diameter of the catheter tube undergoes a significant transition may be particularly suitable for the present invention to relieve the stresses in the transition area of the catheter tube. Similarly, the present invention may be particularly useful with catheter tubing wherein two different diameter portions of catheter tubing are bonded together, where a window is desired along the lumen of the two tubes or even where a repair to the catheter tubing is desired. In these situations, the inner diameter of the proximal portion will be slightly larger than the outer diameter of the catheter tube and also larger than the distal portions. The central section will be larger than both portions of the catheter tube contained therein and the distal portion will be slightly larger than the portion of the catheter tube contained therein and will be smaller than the proximal and central sections of the strain relief device. Preferably both the proximal and distal portions will also include vent areas to allow the bonding agent to flow therein in a uniform and symmetrical manner. As mentioned above, the outer surface of this embodiment of the strain relief device may include a suture wing configuration and also be attached adjacent to the connection of the hub and catheter tube.

In a preferred form of manufacture of the present invention, the central section of the strain relief device is sized to a diameter substantially greater than the catheter tube and the proximal and distal portions are sized to a diameter only slightly greater than the outer diameter of the catheter tube. Additionally, the proximal and distal portions preferably include a slightly tapered or funnel shaped surface on the end portion thereof as well as a vent area for each of the respective distal and proximal portions to facilitate the flow of the bonding material into the distal and proximal portions. Initially, the catheter tube is inserted through the lumen of the strain relief and the strain relief is moved to the desired location along the catheter tube. A bonding material such as a solvent is then applied to either the distal or proximal ends of the strain relief adjacent to the tapered area and vent area. The bonding material is allowed to wick into the interior of the distal or proximal portion and is allowed to flow around the catheter tube and cavity by capillary action. If further bonding material is desired, it may be dispensed into the tapered area. Next, the bonding material may be applied to the tapered area and vent area of the other of the distal or proximal ends. Because of the presence of the vent area, air can escape as the bonding material flows into the cavity and around the catheter tube by capillary action in this second bonding area. The formation of the central section of the lumen of the strain relief to a diameter significantly larger than that of the distal or proximal portion functions to prevent the bonding material from flowing into that area. This is believed to be caused by the preference of the material to flow around the proximal and distal end portions rather than flowing axially into the rapidly increasing surface area of the central section. The bonding material is held in the desired location by the capillary action to surround the catheter tube and lumen of the distal and proximal portions of the strain relief. The presence of the two bonding areas provides a strain relief which is securely bonded to the catheter tube at two locations along the catheter tube. Therefore, the typical stresses encountered during the manufacture and use of the catheter will not adversely affect the operation and function of the catheter of the present invention.

The above and other objects and advantages of the present invention will become apparent from the following detailed description and drawings which are fully descriptive and illustrative of the currently preferred form of the present invention.

DETAILED DESCRIPTION OF THE PREFERRED EMBODIMENTS

Figure 1:
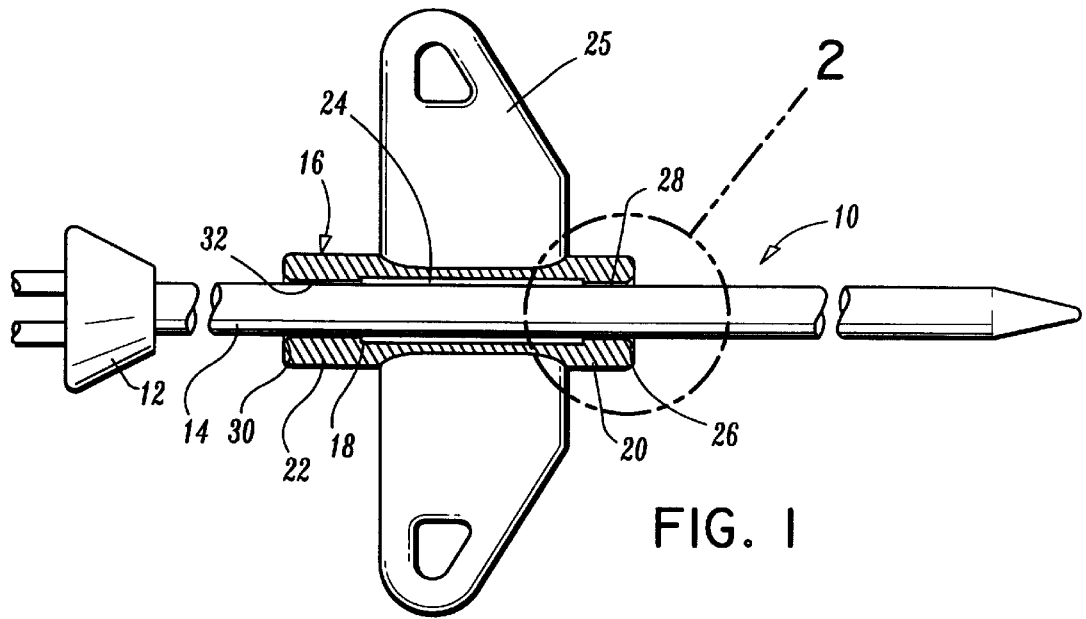
FIG. 1 is a partial cross-sectional view of a catheter and a strain relief device of the present invention showing the catheter in perspective and the strain relief in cross-section.

As shown in FIG. 1, a first preferred form of the present invention is used on a catheter 10 having a hub 12 and catheter tube 14. The strain relief device 16 is preferably formed by an injection molding process and is formed of a material, such as polyurethane and which has a flexibility that is less than that of the catheter tube 14, yet is greater than or equal to the flexibility of the hub 12. The strain relief device 16 includes a lumen 18 extending therethrough. The lumen 18 has a diameter which is sufficient to allow the passage of at least a portion of the catheter tube 14 therethrough to facilitate the assembly thereof. As best shown in FIG. 1, the strain relief device 16 preferably includes a distal portion 20 and a proximal portion 22 as well as a central portion 24 adjacent to the lumen 18. In the preferred form of the present invention, a pair of suture wings 25 extend laterally from the external surface of the strain relief device 16.

Figure 2:
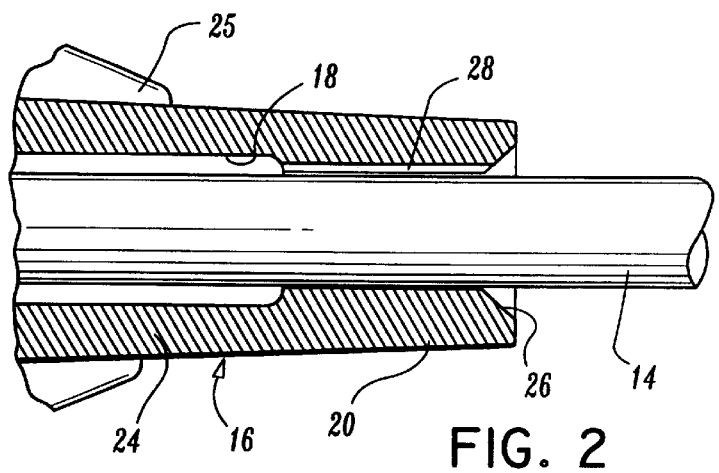
FIG. 2 is an enlarged view of the area labeled "II" in FIG. 1.
Figure 3:
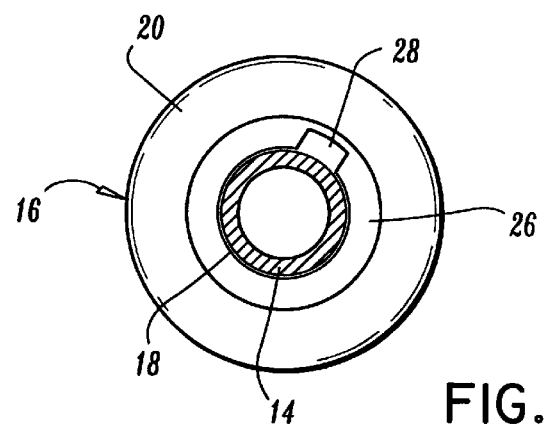
FIG. 3 is an enlarged end view of the distal end of the strain relief device shown in FIG. 1.

In this embodiment, the diameter of the distal portion 20 and the proximal portion 22 are preferably approximately equal to each other and the outer diameter of the portion of the catheter tube 14 which is intended to receive the strain relief device 16 thereon. In the preferred form of the central portion 24, the diameter is preferably about twenty five percent greater than the diameter of the distal portion 20 or proximal portion 22 adjacent to the lumen 18. As shown in FIG. 2, the lumen 18 adjacent to the distal portion 20 includes an outwardly tapered lip 26 extending along the circumference thereof. Additionally, a vent area 28 is formed along the lumen 18 to create a channel for the bonding material to flow into the distal portion. The vent area 28 may consist of one or more channels which extend the entire length of the distal portion 20 to promote the capillary flow of the bonding material into and along the distal portion 20. The presence of at least one vent 28 area on at least one of the distal portion 20 or proximal portion 22 is important in the preferred embodiment due to the existence of two bonding areas. Without the vent area 28, it has been found that when either the distal portion 20 or the proximal portion 22 is bonded, air may not be allowed to escape from the opposite end of the strain relief device and the bonding material may not flow consistently into the other of the distal or proximal portion because the opposite end of the strain relief device is effectively sealed. Therefore, it is preferable that at least the portion of the strain relief device 16 which is to be bonded as a later step in the manufacturing process include a vent area 28.

In this preferred embodiment of the present invention, the proximal portion 22 preferably also includes an outwardly tapered lip 30 and a vent area 32 to promote the flow of the bonding material into the proximal portion 22. The tapered lip 26 and the vent area 28 enable the bonding material to be placed adjacent to the tapered lip 26 on the strain relief device 16 and the bonding material will flow around the lumen of the strain relief device and the around the catheter tube in a preferably uniform and symmetrical manner. The vent area 28 also facilitates the capillary action of the distal portion so that the air is allowed to flow therefrom and the bonding material is drawn into the distal portion 20 such that the bonding material uniformly flows between the catheter tube and the distal portion. The central portion 24 in the strain relief device has the largest diameter of the lumen 18 and therefore allows the air to pass therefrom while the capillary forces draw the bonding material into the respective distal or proximal portions. The flow of the bonding material into the central portion in inhibited by the increased surface area of the central portion as compared to the surface area of the distal or proximal portion. Additionally, the use of the vent area 28 on the distal portion 20 and the vent area 32 on the proximal portion 22 allows the bonding material to flow into the proximal portion 22 when the distal portion 20 has been previously bonded and into the distal portion 20 when the proximal portion 22 has been previously bonded.

The strain relief device 16 of the present invention is designed so that the deflection and flexibility characteristics of the strain relief device remain the same or are improved over prior strain relief devices. These characteristics are important in order to avoid abrupt curvature changes, such as kinking of the catheter and to ensure predictable and uniform curvatures adjacent to the strain relief device. The strain relief device of the present embodiment also provides superior pull to separation forces such that the strain relief device having the suture wings of the preferred embodiment thereon will not separate from the catheter tube unless forces which are substantially greater than those forces that are typically encountered during normal catheter use are applied to the suture wing. Similarly, any torsional forces which are typically encountered during typical catheter use are readily overcome by the catheter strain relief device of the present invention. Additionally, in the event that it is desired to bond two pieces of catheter tubing together at the desired location of the strain relief device 16, the use of the distal portion 20 and proximal portion 22 to form two separate or distinct bonding areas will provide the user with superior pull to separation forces such that the strain relief device will resist kinking as well as separation of the catheter tube if increased lateral, torsional and/or longitudinal forces are applied to the catheter tube. The geometry of the lumen 18 is designed to correlate to the viscosity of the bonding material so that the capillary forces resulting from the placement of the bonding material into the tapered lip of the respective portions will pull the bonding material into a complete, even uniform bonding pattern which at least forms a bond having a radially symmetrical surface about the end of the respective portion and which preferably entirely fills and corresponds precisely with the geometry of the lumen along the outer surface of the catheter tube.

It is anticipated that the geometry of the lumen 18 may be adjusted depending on the intended viscosity and strength of the bonding material used. For example, when a bonding material such as THF is used, it is anticipated that the diameter of the lumen 18 along the distal portion 20 and proximal portion 22 of the strain relief device 16 will be sized to be about two thousandths of an inch larger than the anticipated diameter of the catheter tube. Therefore, with a catheter of about 2.5 french, the catheter tube will be approximately thirty two thousandths of an inch plus or minus two thousandths of an inch. As a result, the diameter of the distal portion 20 and the proximal portion 22 will be about thirty six thousandths of an inch to ensure that there is always about one or two thousandths of an inch of clearance between the lumen 18 and the catheter tube. In this example, the diameter of the central portion 24 will be about forty-five thousandths of an inch. This spacing will promote the capillary action to allow the bonding material such as THX to flow into the distal portion and proximal portion. In the preferred form of the present invention, the length of the distal portion and the proximal portion adjacent to the lumen should be in the range of about twenty to sixty thousands of an inch to ensure sufficient bond strength. The length of the distal portion and proximal portion are preferably limited in order to avoid any negative effect on the deflection and flexibility characteristics of the catheter tube due to the presence of the bond. Another limiting feature on the length of the distal portion and the proximal portion is the desire to avoid the entrapment of the solvent in a manner which prevents proper evaporation of the solvents in the bonding material. If the solvents are not properly evaporated, the trapped unevaporated solvents may degrade the catheter tube and/or strain relief device. Therefore, as the diameter of the catheter tube and bonding material that are to be used is changed, the diameter and length of the distal portion and/or proximal portion are preferably also modified to provide an optimal bonding surface between the catheter tube and/or hub and the interior of the strain relief device.

Figure 4:
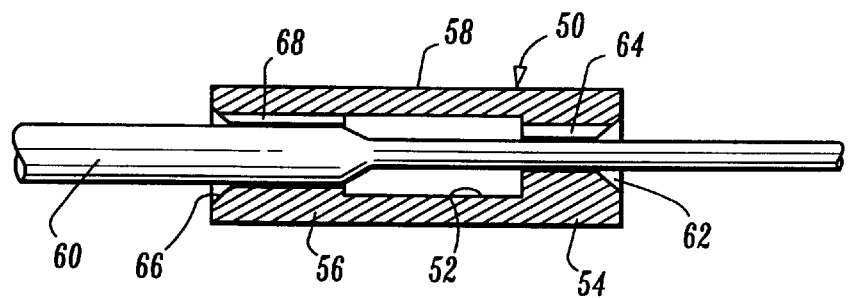
FIG. 4 is a partial cross-sectional view of a bump tubing type of catheter and an alternate form of the strain relief device of the present invention showing the catheter in perspective and the strain relief in cross-section.

As shown in FIGS. 4–7, an alternate preferred form of the present invention is used on a catheter 10 having a hub 12 and a bump type of catheter tube 60 wherein the diameter of the catheter tube varies between the proximal and distal portions thereof. The strain relief device 50 of this embodiment is preferably formed by an injection molding process and is formed of a material, such as polyurethane and which has a flexibility that is less than that of the catheter tube 60, yet is greater than or equal to the flexibility of the hub 12. The strain relief device 50 includes a lumen 52 extending therethrough. The lumen 52 has a minimum diameter which is sufficient to allow the passage of at least a portion of the catheter tube 60 therethrough to facilitate the assembly thereof. As best shown in FIG. 4, the strain relief device 50 preferably includes a smaller diameter distal portion 54 and a larger diameter proximal portion 56 as well as an even larger diameter central portion 58 adjacent to the lumen 52.

In this embodiment, the diameter of the distal portion 54 and the proximal portion 56 are preferably approximately equal to the outer diameter of the portion of the catheter tube 60 which is intended to receive the strain relief device 50 thereon. As shown, the lumen 52 adjacent to the distal portion 54 includes an outwardly tapered lip 62 extending along the circumference thereof. Additionally, a vent area 64 is formed along the lumen 52 to create a channel for the bonding material to flow into the distal portion 54. The vent area 64 may consist of one or more channels which extend longitudinally along the entire lengthwise dimension of the distal portion 54 to promote the capillary flow of the bonding material into and along the distal portion 54. The presence of at least one vent area on either the distal portion 54 or proximal portion 56 is important in the present embodiment due to the existence of the two bonding areas along the catheter tube. Without at least one vent area, it has been found that when either the distal portion 54 or the proximal portion 56 is bonded, the bonding material may not flow consistently into the second portion because the opposite end of the strain relief device is sealed and may not allow the air in the lumen to flow therefrom. Therefore, it is preferable that at least the portion of the strain relief device 50 which is to be bonded as a later step in the manufacturing process include a vent area.

Figure 5:
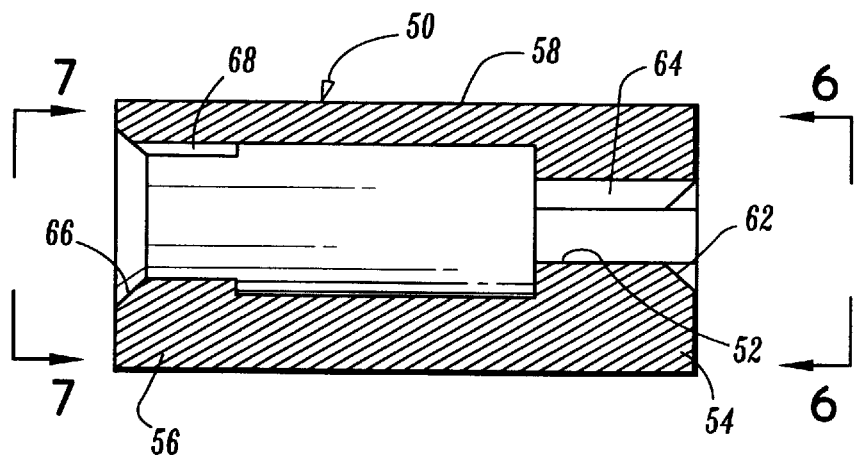
FIG. 5 is an enlarged cross-sectional view of the strain relief device of FIG. 4.
Figure 6:
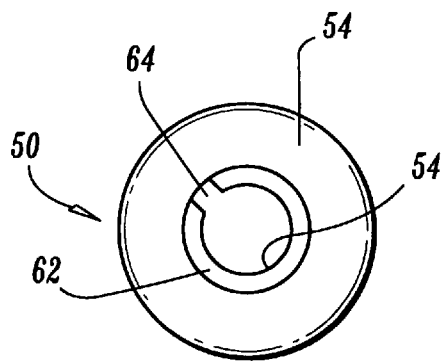
FIG. 6 is an enlarged end view of the distal end of the strain relief device shown in FIG. 4.
Figure 7:
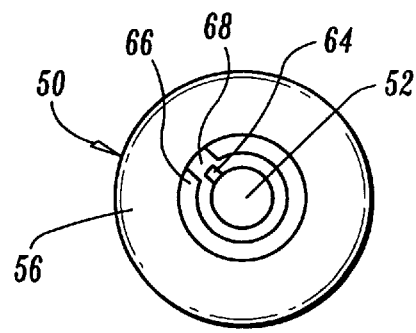
FIG. 7 is an enlarged end view of the proximal end of the strain relief device shown in FIG. 4.

As best shown in FIG. 5, the proximal portion 56 preferably also includes an outwardly tapered lip 66 and a proximal vent area 68 to promote the flow of the bonding material into the proximal portion 56. The tapered lip 66 and the vent area 68 enable the bonding material to be placed adjacent to the tapered lip 66 on the strain relief device 50 and the bonding material will flow around the lumen of the strain relief device 50 and the around the catheter tube 60. The proximal vent area 68 also facilitates the capillary action of the distal portion so that the bonding material is drawn into the distal portion 54 as the air flows outwardly therefrom so that the bonding material uniformly flows between the catheter tube and the distal portion. The central portion 58 in the strain relief device has the largest diameter portion of the lumen 52 and therefore allows the capillary forces to draw the bonding material into the respective distal or proximal portions while inhibiting the flow of the bonding material into the central portion. As described above, this is believed to be due at least in part to the differences in the surface area of the distal or proximal areas and the central portion. In a preferred form of this embodiment, the diameter of the central portion is preferably significantly larger than the diameter of the proximal portion 56. Additionally, the use of the vent area 64 on the distal portion 54 and the vent area 68 on the proximal portion 56 allows the bonding material to flow into the proximal portion when the distal portion 54 has been previously bonded and into the distal portion when the proximal portion has been previously bonded to the catheter tube and/or hub.

The strain relief device 50 of this embodiment is designed so that the deflection and flexibility characteristics of the strain relief device remain the same or are improved over prior strain relief devices. These characteristics are important in order to avoid abrupt curvature changes, such as kinking of the catheter and to ensure predictable and uniform curvatures adjacent to the strain relief device. The strain relief device of the present embodiment also provides superior pull to separation forces such that the strain relief device of this embodiment having suture wings similar to those of the preferred embodiment will not separate from the catheter tube unless forces which are substantially greater than those forces that are typically encountered during normal catheter use are applied to the suture wing. It is believed that any such excess forces would overcome the wing portions of the suture wings before the strain relief of the present invention were overcome.

Figure 10:
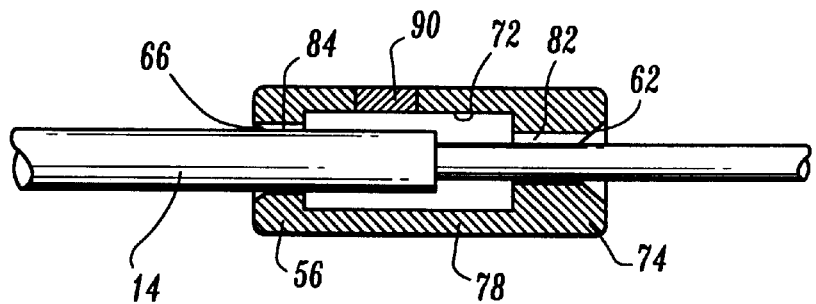
FIG. 10 is a partial cross-sectional view of two different diameter portions of a catheter tube and an alternate form of the strain relief device of the present invention showing the catheter tube in perspective and the strain relief in cross-section.

Additionally, the present invention may also be used in the event that it is desired bond the catheter strain relief device to the hub and catheter tube (FIGS. 8 and 9) or to bond two pieces of catheter tubing having different diameters together at the desired location of the strain relief device 50 (FIG. 10). The use of the different diameter distal portion 54 and proximal portion 56 to form two bonding areas will provide the user with superior pull to separation forces such that the strain relief device will resist kinking due to various torsional forces as well as resistance to the separation of the separate sections of catheter tube if increased lateral, torsional and/or longitudinal forces are applied to the catheter tube.

The geometry of the lumen 52 is designed to correlate to the viscosity of the bonding material so that the capillary forces resulting from the placement of the bonding material into the tapered of the respective portions will pull the bonding material into a complete, even uniform bonding pattern which at least forms a bond having a radially symmetrical surface about the end of the respective portion and which preferably entirely fills and corresponds precisely with the geometry of the lumen along the catheter tube.

It is anticipated that the geometry of the lumen 50 of this embodiment may also need to be adjusted according to the viscosity and strength of the bonding material used. For example, when a bonding material such as THF is used, it is anticipated that the diameter of the lumen 52 along the distal portion 54 and proximal portion 56 of the strain relief device 50 will be sized to be about two thousandths of an inch larger than the anticipated diameter of the adjacent portion of the catheter tube. Therefore, with a catheter tube having a distal segment of about 2.5 french, the diameter of the distal segment of the catheter tube will be approximately thirty two thousandths of an inch plus or minus two thousandths of an inch. As a result, the diameter of the distal portion 54 of the strain relief device will be about thirty six thousandths of an inch to ensure that there is always about one or two thousandths of an inch of clearance between the lumen 52 and the distal segment of the catheter tube. In this example, the catheter tube also has a proximal segment of about 5 french and the diameter of the proximal segment of the catheter tube will be approximately sixty five thousandths of an inch plus or minus two thousandths of an inch. As a result, the diameter of the proximal portion 56 of the strain relief device 50 will be about sixty eight thousandths of an inch to ensure that there is always about one or two thousandths of an inch of clearance between the lumen 52 and the proximal segment of the catheter tube. In this example, the diameter of the central portion 58 will preferably be about seventy five thousandths of an inch. This spacing will promote the capillary action to allow the bonding material such as THX to flow into the distal portion and proximal portions of the strain relief device 50. In the preferred form of the present invention, the length of the distal portion and the proximal portion adjacent to the lumen should be in the range of about twenty to sixty thousands of an inch to ensure sufficient bond strength. The length of the distal portion and proximal portion are preferably limited in order to avoid any negative effect on the deflection and flexibility characteristics of the catheter tube due to the presence of the bond. Another limiting feature on the length of the distal portion and the proximal portion is the desire to avoid the entrapment of the solvent in a manner which prevents proper evaporation of the solvents in the bonding material. If the solvents are not properly evaporated, the trapped unevaporated solvents may degrade the catheter tube and/or strain relief device. Therefore, as the diameter of the catheter tube and bonding material that are to be used is changed, the diameter and length of the distal portion and/or proximal portion must also be modified to provide the optimal bonding surface.

Figure 8:
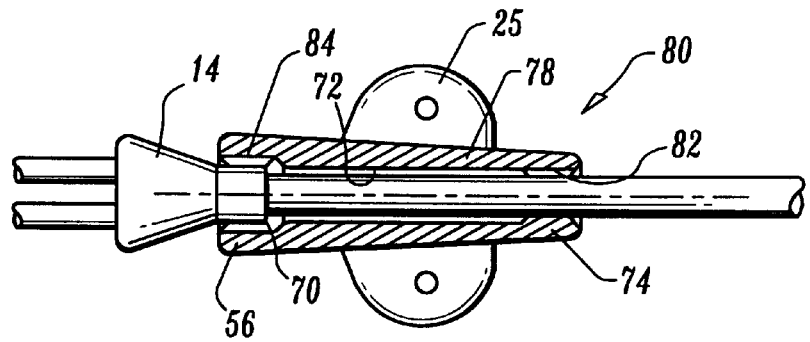
FIG. 8 is a partial cross-sectional view of the connection between the hub member and catheter tube and an alternate form of the strain relief device of the present invention showing the hub and catheter tube in perspective and the strain relief in cross-section.
Figure 9:
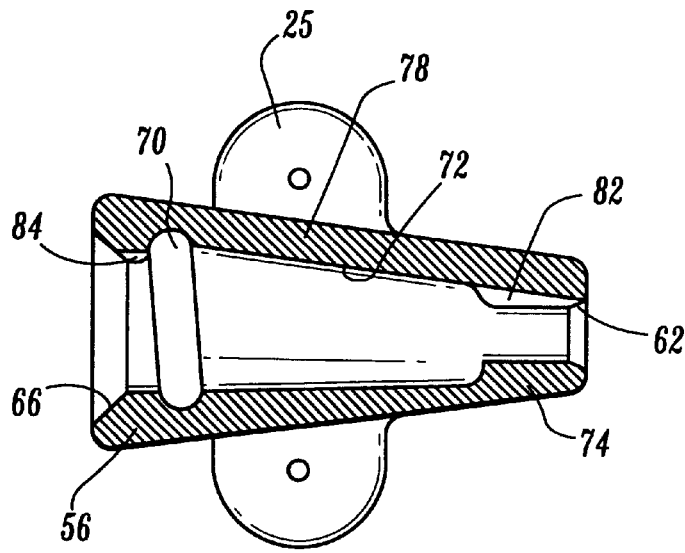
FIG. 9 is a partial cross-sectional view of the embodiment shown in FIG. 8 with the hub member and catheter tube removed.

The embodiment illustrated in FIG. 8 includes an additional intermediate portion 70 which has a diameter which is greater than the diameter of the lumen 72 adjacent to the distal portion 74, proximal portion 76 and the central portion 78. As shown, the intermediate portion 70 forms an enlarged diameter area which inhibits the flow of bonding material inwardly beyond the proximal portion 76. Additionally, in this embodiment, the central portion 78 has a diameter which gradually increases from the distal portion 74 towards the intermediate portion 70 and is in between the diameters of the distal portion 74 and the proximal portion 76. Additionally, in this embodiment, the strain relief device 80 includes a pair of vent areas 82 and 84, respectively, which extend longitudinally along the interior of the distal portion 74 and proximal portion 76. The function of this embodiment of the present invention is substantially similar to the embodiments described above and, therefore, will not be separately referred to herein.

The embodiment illustrated in FIG. 10 includes a preferably transparent or semi-transparent window 90 as an additional feature which may be readily incorporated into the embodiments of the strain relief devices described above. As shown in FIG. 10, the window preferably is located on a section of the central portion 78 which has a lumen diameter that is greater than the diameter of the lumen 72 adjacent to the distal portion 74 or proximal portion 76. The window 90 is preferably in fluid flow communication with at least one inner lumen of the catheter tube although it is anticipated that the window 90 may be partitioned (not shown) or otherwise modified to enable the user to observe the flow of fluids through one or more lumens of the catheter The function of this embodiment of the present invention is substantially similar to the embodiments described above and, therefore, will not be separately referred to herein.

It will be apparent from the foregoing that, while the preferred embodiments of the invention relate to the use of the invention with catheters, various other general uses of the invention in conjunction with other types of tubular devices are anticipated, including modifications to the presently preferred embodiments, without departing from the spirit and scope of the present invention. Accordingly, it is not intended that the invention be limited in any manner, except as by the appended claims.

What is claimed is:

1. A strain relief device for relieving strain concentration along a flexible medical device member, said strain relief device comprising:

a strain relief body having a proximal portion, a central portion and a distal portion, said strain relief body including a longitudinal dimension and forming a lumen extending therethrough and the flexible medical device member being positionable through said lumen;

means for attaching said distal portion of said strain relief body to the flexible medical device member, and including a vent are extending longitudinally along said distal portion and located between said distal portion and the flexible medical device member, said vent area including means for encouraging bonding of a material therein to said strain relief body and the flexible medical device member;

means for discouraging bonding of a material between said strain relief body and the flexible medical device member in said central portion of said strain relief body; and whereby said device inhibits strain concentrations due to lateral-type forces which tend to bend the flexible medical device member at an angle relative to a longitudinal dimension thereof and due to axial pull forces which tend to separate said strain relief body from the flexible medical device member.

2. The strain relief device of claim 1 wherein said means for discouraging bonding further includes a variation in the diameter of said lumen between the diameter of said lumen adjacent to said distal portion and the diameter of said lumen adjacent to said central portion.

3. The strain relief device of claim 1 wherein said means for discouraging bonding further includes a variation in the diameter of said lumen between the diameter of said lumen adjacent to said proximal portion and the diameter of said lumen adjacent to said central portion.

4. The strain relief device of claim 1 wherein said means for attaching further includes a variation in the diameter of said lumen between the diameter of said lumen adjacent to said distal portion and the diameter of said lumen adjacent to said central portion.

5. The strain relief device of claim 1 wherein said distal portion includes a distal end thereon and said distal end includes a tapered surface thereon which extends radially outwardly from said lumen and said tapered surface forms at least part of said means for bonding.

6. The strain relief device of claim 1 wherein said means for attaching further includes a variation in the diameter of said lumen between the diameter of said lumen adjacent to said distal portion and the diameter of said lumen adjacent to said proximal portion.

7. The strain relief device of claim 1 wherein said means for discouraging bonding further includes a variation in the diameter of said lumen between the diameter of said lumen adjacent to said distal portion and the diameter of said lumen adjacent to said central portion.

8. The strain relief device of claim 1 wherein said means for bonding causes the bonding material to form a bilaterally symmetrical bond between said distal portion and said flexible medical device member.

9. The strain relief device of claim 1 wherein said means for bonding causes the bonding material to form a bilaterally symmetrical bond between said proximal portion and said flexible medical device member.

10. The strain relief device of claim 1 wherein said means for bonding causes the bonding material to form a bilaterally symmetrical bond between said distal portion and said flexible medical device member and said proximal portion and said flexible medical device member.

11. The strain relief device of claim 1 wherein said strain relief body inhibits the application of torsional forces to said flexible medical device.

12. A strain relief device for relieving strain concentration along a flexible medical device member, said strain relief device comprising:

a strain relief body having a proximal portion, a central portion and a distal portion, said strain relief body including a longitudinal dimension and forming a lumen extending therethrough and at least a portion of the flexible medical device member being positionable through said lumen and sized to extend through said lumen;

means for attaching said distal portion of said strain relief body to the flexible medical device member, and including a vent area extending longitudinally along said distal portion and located between said distal portion and the flexible medical device member, said vent area including means for encouraging bonding of a material therein to said strain relief body and the flexible medical device member;

means for attaching said proximal portion of said strain relief body to the flexible medical device member, and including a vent area extending longitudinally along said proximal portion and located between said proximal portion and the flexible medical device member, said vent area including means for encouraging bonding of a material therein to said strain relief body and the flexible medical device member;

means for discouraging bonding of a material between said strain relief body and the flexible medical device member in said central portion of said strain relief body and whereby, said device inhibits strain concentrations due to torsional-type forces which tend to bend, twist and/or kink the flexible medical device member.

13. The strain relief device of claim 12 wherein said means for discouraging bonding further includes a variation in the diameter of said lumen between the diameter of said lumen adjacent to said distal portion and the diameter of said lumen adjacent to said central portion.

14. The strain relief device of claim 12 wherein said means for discouraging bonding further includes a variation in the diameter of said lumen between the diameter of said lumen adjacent to said proximal portion and the diameter of said lumen adjacent to said central portion.

15. The strain relief device of claim 12 wherein the diameter of said lumen adjacent to said proximal portion is approximately equal the diameter of said lumen adjacent to said distal portion.

16. A strain relief device for relieving strain concentration along a flexible medical device member, said strain relief device including a suture wing thereon and comprising:

a strain relief body having a proximal portion, a central portion and a distal portion, said strain relief body including a longitudinal dimension and forming a lumens extending therethrough and the flexible medical device member being positionable through said lumen;

means for attaching said distal portion and said proximal portion of said strain relief body to the flexible medical device member, and at least one of said distal portion and said proximal portion including a vent area extending longitudinally along said at least one of said distal portion and said proximal portion and said vent area being located between said at least one of said distal portion and said proximal portion and the flexible medical device member, said vent area including means for encouraging bonding of a material therein to said strain relief body and the flexible medical device member;

means for discouraging bonding of a material between said strain relief body and the flexible medical device member in said central portion of said strain relief body; and whereby said device inhibits strain concentrations due to lateral-type forces which tend to bend the flexible medical device member at an angle relative to a longitudinal dimension thereof and due to axial pull forces which tend to separate said strain relief body from the flexible medical device member.

17. The strain relief device of claim 16 wherein said means for discouraging bonding further includes a variation in the diameter of said lumen between the diameter of said lumen adjacent to said distal portion and the diameter of said lumen adjacent to said central portion.

18. The strain relief device of claim 16 wherein said means for discouraging bonding further includes a variation in the diameter of said lumen between the diameter of said lumen adjacent to said proximal portion and the diameter of said lumen adjacent to said central portion.

19. The strain relief device of claim 16 wherein the diameter of said lumen adjacent to said proximal portion is greater than the diameter of said lumen adjacent to said distal portion.

20. The strain relief device of claim 16 wherein the diameter of said lumen adjacent to said proximal portion is approximately equal to the diameter of said lumen adjacent to said distal portion.

21. A strain relief device for relieving strain concentration along a flexible medical device member, said strain relief device comprising:

a strain relief body having a proximal portion, a central portion and a distal portion, said strain relief body including a longitudinal dimension and forming a lumen extending therethrough and the flexible medical device member being positionable through said lumen;

bonding material for attaching said distal portion of said strain relief body to the flexible medical device member, and including a vent area extending longitudinally along said distal portion and located between said distal portion and the flexible medical device member, said vent area including an area for encouraging bonding of a material therein to said strain relief body and the flexible medical device member;

an area for discouraging bonding of a material between said strain relief body and the flexible medical device member in said central portion of said strain relief body; and a window area along said central portion to enable the user to observe the flow of fluids therethrough.

* * * * *